United States Patent [19]

Beremand et al.

[11] Patent Number: 5,087,563
[45] Date of Patent: Feb. 11, 1992

[54] ACYL CARRIER PROTEIN-I/PROTEIN-A GENE FUSION, PRODUCTS AND METHODS

[75] Inventors: Phillip D. Beremand, Peoria, Ill.; Daniel J. Guerra, Troy, Id.

[73] Assignee: The United States of America, as represented by the Secretary of Agriculture, Washington, D.C.

[21] Appl. No.: 494,004

[22] Filed: Mar. 9, 1990

[51] Int. Cl.$^5$ .................. C12P 21/02; C12N 15/62; C07K 3/00
[52] U.S. Cl. ........................ 435/69.7; 536/27; 435/172.3; 435/320.1; 530/370
[58] Field of Search ............... 435/69.7, 172.3; 530/350, 412

[56] References Cited

PUBLICATIONS

Arch. Biochem. Biophys. 256:90–100, Jul. 1987, Beremand et al., Synthesis, Cloning and Expression in Eschericlaia Coli of a Spinach Acyl Carrier Protein-I Gene.
EMBO J. 4:1075–1080, 1984, Nilsson et al. Immobilization and Purification of Enzymes with Staphylococcal Protein A gene fusion Vectors.
John B. Ohlrogge et al., "Acyl Carrier Protein: Central Cofactor for Plant Fatty Acid Metabolism," What's New in Plant Physiology 15(11): 41–44 (Nov. 1984).
Katherine M. Schmid et al., "A Root Acyl Carrier Protein-II from Spinach is Also Expressed in Leaves and Seeds," Plant Mol. Biol. 15: 765–778 (1990).
John B. Ohlrogge, Table: "ACP% Protein Identity," personal communication to Phillip D. Beremand.

*Primary Examiner*—Richard A. Schwartz
*Assistant Examiner*—John D. Ulm
*Attorney, Agent, or Firm*—M. Howard Silverstein; John D. Fado; Curtis P. Ribando

[57] ABSTRACT

A gene encoding spinach acyl carrier protein-I-Gly$^{76}$ (ACP-I) was fused to a gene encoding the F$_c$-binding portion of staphylococcal protein A. The gene fusion can be expressed in E. coli thereby resulting in the production of an appropriately sized protein possessing ACP activity in acyl ACP synthetase reactions, plant MCT reactions, and plant fatty acid synthesis. This gene fusion, under the control of the $\lambda P_R$ promoter, expresses high levels of a 42 kDa fusion protein in *E. coli*. This protein functions as a affinity moiety in purification methods for the isolation of enzymes involved in fatty acid synthetase, acyl ACP synthetase and malonyl-CoA:ACP tranacylase reactions.

20 Claims, 7 Drawing Sheets

ACYL CARRIER PROTEIN-I/PROTEIN-A GENE FUSION, PRODUCTS AND METHODS

BACKGROUND OF THE INVENTION

1. Field of the Invention

This invention relates to the construction and expression of gene fusions encoding a functional spinach acyl carrier protein-I (ACP-I) and the $F_c$-binding portion of staphylococcal protein A. Additionally this invention relates to methods for the purification of enzymes participating in fatty acid synthetase (FAS) reactions.

2. Description of the Prior Art

Heretofor there has been difficulty in isolating and purifying FAS enzymes, particularly malonyl-CoA: Acyl Carrier Protein (ACP) transacylase (MCT) [Guerra, et al., Arch. Biochem. Biophys., Vol. 246, (1986), pp. 274–285].

Gene fusions encoding hybrid eukaryotic to prokoryotic proteins have been shown to stabilize as well as protect these proteins from proteolysis during expression in Escherichia coli (E. coli) [Davis, et al., Proc. Natl. Acad. Sci. USA, Vol. 78, (1981), pp. 5376–5380; Goeddel, et al., Proc. Natl. Acad. Sci. USA, Vol. 76, (1979), pp. 106–110 and Itakura, et al., Science, Vol. 49, (1984), pp. 483–492]. Fusions of this type can result in a higher level of eukaryotic protein production. Furthermore fusion to proteins such as beta-galactosidase or staphylococcal protein A allows for the affinity purification of the fusion protein [Geronimo, et al., Proc. Natl. Acad. Sci., USA, Vol. 80, (1983), pp. 6848–6852 and Nilsson, et al., EMBO J, Vol. 4, (1985), pp. 1075–1080]. The fusion of small proteins and peptides to larger proteins using recombinant DNA techniques serves ideally as an alternative to chemical coupling.

In plants ACP exists as a small acidic cofactor protein which participates in at least 12 reactions of fatty acid biosynthesis and metabolism and occurs in at least 2 isoforms (ACP I and ACP II) in several plants [Hoj PB, S. I., Carlsberg Res. Commun., Vol. 49 (1984), pp. 483–492; Ohlrogge, et al., The Biochemistry of Plants, Stumpf, P. K. (ed), Vol. 9, pp. 137–157, Academic Press, Orlando, Fla., (1987); Ohlrogge, et al., J. Biol. Chem., Vol. 260, (1985), pp. 8032–8037 and Ullman, A., Gene, Vol. 29, (1984), pp. 27–31]. In recent years, research on this protein has intensified because of the potential of ACP to serve as a representative marker protein for studies of the regulation of plant fatty acid synthetase gene expression. The cloned gene encoding spinach ACP-I has been sequenced [Beremand, et al., Arch. Biochem. Biophys., Vol. 256, (1987), pp. 90–100] and the subject of the current investigations.

In light of the prior art it can be seen there is a need for efficient methods by which proteins participating in fatty acid biothsynthesis may be identified and purified.

SUMMARY OF THE INVENTION

It is an object of the present invention to provide a hybrid protein comprising ACP and the $F_c$-binding portion of staphytococcal protein A. It is another object of the invention to provide recombinant DNA molecules comprising genes encoding for the hybrid protein. Still another object is to provide methods for affinity purification of enzymes involved in fatty acid biosynthesis.

A gene encoding for spinach ACP-I is fused to a gene encoding the $F_c$-binding portion of staphylococcal protein A. The resulting gene fusion is under the control of the $P_R$ promoter and expressed at high levels in E. coli producing a 42 kDa fusion protein. The fusion protein is phosphopantethenylated in E. coli. In vitro analysis of the ACP portion of the fusion protein shows activity by participating in acyl ACP synthetase, plant malonyl-CoA:ACP transacylase reactions and FAS reactions. Unexpectedly, the hybrid protein is more effective in product formation than the wild type enzyme (see FIG. 6).

Enzymes involved in these reactions can be purified by affinity chromatography techniques using the hybrid fusion protein.

BRIEF DESCRIPTION OF THE DRAWINGS

FIG. 1. Western blot analysis of ACP fusion protein. Cultures of N4830-1 carrying pPB3, pRIT2T, or no plasmid were grown and induced as described in the detailed description of the invention. Cells from both uninduced and induced cultures were boiled in sample buffer and loaded onto a 15% SDA-polyacrylamide gel. Following electrophoresis the proteins were electroblotted to nitrocellulose and probed with anti-spinach ACP-1 antibody (from rabbits) which has been blocked with E. coli extract to prevent interactions with E. coli ACP. Bound rabbit antibody was visualized with alkaline phosphatase-linked anti-rabbit antibody. The individual lanes contained: 1, uninduced pPB3-carrying cells; 2, induced pPB3-carrying cells; 3, uninduced pRIT2T-carrying cells; 4, induced pRIT2T-carrying cells; 5, uninduced N4830-1 cells (no plasmid); 6, induced N-4830-1 cells.

FIG. 2. SDS-PAGE analysis of IgG sepharose-purified products. Induced cultures (10 ml) of N4830-1 cells carrying pPB3, pRIT2T, or no plasmid were lysed and subjected to IgG sepharose chromatography. In each case, 0.25 ml of the 0.5 ml elution fraction from the column was lyophilized and then resuspended in 50 μl of sample buffer, on which 25 μl were loaded onto 15% SDS-polyacrylamide gels. The gel was subsequently stained with Coomassie Blue. Lane 1 contains the IgG Sepharose-purified material from N4830-1 cells carrying no plasmid; lane 2, the eluted proteins from cells carrying pPB3; lane 3, the eluted proteins from pRIT2T; lane 4 contains 10 μg of ovalbumin.

FIG. 3. B-alanine labelling of the fusion protein. Cells were grown at 30° C. in the presence of 66 μCi/ml of [3-H] B-alanine to an $OD_{550}$ of 0.5, then thermally induced. Samples were taken just prior to and 90 min. after induction. Cell pellets were boiled in sample buffer and subjected to electrophoresis of a 10% SDS-polyacrylamide gel. A fluorogram was prepared from the dried gel. Lanes 1–3 contain samples taken just prior to induction. Lanes 4–6 contain samples taken after thermal induction. Lanes 1 and 4 are from cells carrying pPB3, lanes 2 and 5 are from cells carrying pRIT2T; lanes 3 and 6 are from cells carrying no plasmid.

FIG. 4. Acyl ACP synthetase reaction products. Cultures of N4830-1 (2.5 ml) carrying pPB3, pRIT2T, or no plasmid were grown, induced, extracted, and subjected to IgG Sepharose chromatography. In each case the first 0.5 ml fraction from the column was lyophilized. The lyophilized samples were resuspended in 50 μl of water. An equivalent portion (4 μl) of each sample was used as an ACP source in acyl ACP synthetase reactions. $^{14}C$-labeled palmitic acid was employed as substrate in the reactions. The reaction products were subjected to electrophoresis on 10% SDS-polyacrylamide gels. A fluorogram was prepared from the gel. Lane, pPB3; lane 2, pRIT2T; lane 3, N4830-1 (no plasmid).

FIG. 5. Acyl ACP synthetase activity. Reactions were carried out as previously described [Stumpf, P. K., "Fatty acid biosynthesis in higher plants". In: Numa, S. (ed.), Fatty Acid Metabolism and its Regulation, (1984), Elsevier, Amsterdam, pp. 155-199] with [1-$^{14}$C] palmitic acid as substrate. Incorporation of label into TCA-precipitatable material was measured in reactions using the purified ACP/protein A fusion (●) or E. coli ACP (○).

FIG. 6. Fatty acid synthetase activity. In vitro FAS reactions were carried out with spinach leaf extracts. The ACP source was either the purified ACP/protein A fusion protein (●) or the purified ACP encoded by the synthetic ACP gene on the plasmid pPB104 (○).

DETAILED DESCRIPTION OF THE INVENTION

Glossary

For the purposes of this invention, the following standard abbreviations and terms used herein are defined below. Additionally, included are a listing of restriction enzymes and an appendix of biological materials described in the specification.

Abbreviations

A:ACP-I = protein A: acyl carrier protein-I
ACP = acyl carrier protein
ACP-I = acyl carrier protein, isoform I
ACP-II = acyl carrier protein, isoform II
bp = base pairs
cI857 = temperature sensitive mutant form of the cI repressor of bacteria phage lambda
cDNA = single-stranded DNA complementary to a messenger RNA
DNA = deoxyribonucleic acid
DIT = dithiothreitol
EDTA = ethylene diamine tetraacetic acid
FAS = fatty acid synthetase
HPLC = high pressure liquid chromatography
IgG = immunoglobulin G
MCT = malonyl-CoA:ACP transacylase
MES = 4-morpholine ethane sulfonic acid
OD = optical density
$P_R$ = high level promotor from bacteria phage
RNA = ribonucleic acid
SDS-Page = sodium dodecyl sulphate polyacrylamide gel electrophoresis
TST = 0.05% v/v tween 20, 50 μM Tris Cl pH 7.6, 150 μM NaCl

Terms clone: in reference to DNA, the product or process of isolating a segment of DNA, linking it to a vector, and introducing it into a host for expression
construct: a DNA molecule produced via recombinant DNA techniques
expression: the transcription of a gene into messenger RNA (mRNA) and the subsequent translation of the mRNA into a protein coded by the gene
expression vector: a DNA sequence such as an amplicon, phage, or plasmid which is able to replicate in a hose cell and express genes present in the DNA sequence
gene: a segment of DNA which encodes a specific protein or polypeptide, or RNA
phage: a bacteriophage; a virus which infects bacteria
plasmid: circular double-stranded DNA capable of autonomous replication within a bacterium
promoter: a recognition sequence for binding of RNA polymerase
repressor: a protein which blocks transcription of gene by binding to a specific region of DNA
subclone: in reference to DNA, the product or process of cloning a portion of an already cloned DNA segment
transcription: the formation of an RNA molecule upon a DNA template by complimentary base pairing mediated by by RNA polymerose
transform: to change in a heritable manner the characteristics of a host cell in response to DNA foreign to that cell
transgenic: relating to new genetic information becoming embedded into a germline
vector: a nucleic acid molecule such as a plasmid or phage and having a site for inserting a gene of interest for cloning, transfer, or expression

| Restriction Enzyme | Cleavage Site |
|---|---|
| BamHI | 5'...G GATCC...3' |

| Appendix of Biological Materials | Source |
|---|---|
| E. coli cells: N4830-1 | Pharmacia |
| Enzymes: | |
| T4 (polynucleotide kinase) | N.E. Biolabs or BRL |
| T4 (DNA ligase of bacteriophage) | IBI |
| Calf intestinal phosphate | Boerhinger |
| Phasmids and Phage: | |
| pPB104 | NRRL B-18218 |
| pPB269 | NRRL B-18219 |
| pRIT2T | Pharmacia |

EXAMPLE I

DNA Constructions

Restriction enzymes were used according to the supplier's recommendations. Ligation of electrophoretically separated DNA fragments was performed in melted IMP agarose [Struhl, K., BioTechiques, Vol. 3 (1985), pp. 452-453] with T4 DNA ligase. Prior to transformation the reaction mixture in melted agarose was diluted with 5 volumes of 5 mM Tris-Cl, 0.5 mM EDTA pH 7.6.

Transformations

Transformations were carried out according to the transformation protocol of Hanahan in the standard transformation buffer [Hanahan, C. L., DNA Cloning, Vol. 1, pp. 109-136, Glover D. (ed.), IRL Press, Washington, D.C., (1985), incorporated herein by reference] except that the recipient cells were grown at 30° C. instead of 37° C.

Induction of IgG Sepharose Chromatography of Fusion Protein

Expression of the fusion protein was induced by growing N4830-1 cells carrying the plasmid pPB3 at 30° C. to an $OD_{550}$ and then adding an equal volume of growth medium heated to 54° C. [Zabeau, et al. EMBO J., Vol. 1 (1982), pp. 1217–1224].

After 90 min. of incubation at 42° C. the cells were harvested by centrifugation. Cell pellets were resuspended in 50 mM Tris-Cl pH 7.5, 1 mM $MgCl_2$, 100 g/ml lysozyme (Sigma) and 4 g/ml DNase I (Sigma). The resuspended cells were subjected to three freeze/thaw cycles, followed by sonication. Cell debris was removed by centrifugation.

The crude lysate was applied to an IgG sepharose 6FF (Pharmacia) column that had been prewashed with 3 bed volumes of each of the following solutions in the order given:
(1) 0.5M acetic acid, pH 3.4
(2) 50 mM Tris-Cl pH 7.6, 150 mM NaCl, and 0.05% Tween 20 (TST)
(3) 0.5M acetic acid;
(4) TST The loaded column was washed with 10 bed volumes of TST followed by 2 bed volumes of 5 mM ammonium acetate, pH 5.0. The fusion protein was eluted with 0.5M acetic acid pH 3.4. Eluted samples were lyophilized.

Purification of Protein A-acyl Carrier Protein-I Fusion Protein

The purification of fusion protein was accomplished by combining the method for purifying plasmid encoded spinach ACP-I from *E. coli* [Guerra, et al., J. Biol. Chem., vol. 263, (1988), pp. 4386–4391, incorporated herein by reference] with IgG sepharose chromatography as described above.

Essentially, *E. coli* cells (N48030-1) carrying the plasmid pPB3 were grown overnight, harvested by centrifugation, and taken up in 10 volumes of 0.1M Tris, 20 mM glycine, 1 mM EDTA, and 2 mM dithiothreitol (DTT) (pH 7.0). The cells were dispersed with a polytron homogenizer and subjected to treatment with lysozyme (0.01 mg/ml) and Triton X-100 (0.17%). The treated cells were then homogenized with a polytron at high speed. A cell-free supernate was obtained after 20 min of centrifugation at $10,000 \times g$. Ammonium sulfate was added to this supernate to 60% of saturation. This mixture was again centrifuged ($8,000 \times g$ for 45 min) and the supernate adjusted to 20% trichloroacetic acid (TCA). Following overnight incubation at 4° C. the mixture was centrifuged at $10,000 \times g$ for 20 min. The derived pellet, containing the fusion protein, was solubilized in 10 mM 4' morpholine ethane sulfonic acid (MES) and 2 mM DTT (pH 6.1). This solution was dialyzed twice against 100 volumes of the solubilization buffer, yielding a cloudy preparation. This was centrifuged for 20 min at $12,000 \times g$ and the cleared supernate was applied to a DEAE (Whatman) column. The column was developed with a 0.1–0.7M LiCl gradient. Active fractions were pooled and brought to 70% ammonium sulfate saturation. The supernate obtained after 20 min of centrifugation at $10,000 \times g$ was brought to 5% TCA and again incubated overnight at 4° C. The fusion protein was precipitated, solubilized and dialyzed as above. The resulting solution was injected onto a preparative HPLC TSK-3000 gel permeation column (Genechem). Active fractions were again pooled and applied to an IgG sepharose column as described above. The final protein preparation was judged to be about 90% pure based on sodium dodecyl sulfate polyacrylamide gel electrophoresis (SDS-PAGE) and Western blotting.

Western Blot Analysis of Fusion Protein Production

Cell extraction, SDS-PAGE, transfer of proteins from gel to nitrocellulose, and binding of rabbit antibody to the ACP moiety of the fusion protein were performed as previously described [Beremand, et al., Arch. Biochem. Biophys., Vol. 256, (1987), pp. 90–100]. Bound rabbit antibody was visualized with the Proto-Blot system purchased from Promega Biotec.

Acyl ACP Synthetase Reaction

Acyl ACP synthetase reactions were carried out as described by [Kuo, et al., Anal. Biochem., Vol. 136, (1984), pp. 479–502] with [9, 10-$^3$H(N)] palmitic acid or [1-$^{14}$C] palmitic acid (New England Nuclear). Completed reactions were loaded directly onto SDS-polyacrylamide gels. After elecrophoresis the were dried, treated with En$^3$hance (New England Nuclear), and used to expose X-Omat AR film (Kodak).

Malonyl-CoA:ACP Transacylase Assays (MCT)

MCT was assayed as previously described [Guerra, et al., Arch. Biochem. Biophys., Vol. 246, (1986), pp. 274–285]. It was isolated from plastids derived from sunflower (*Helianthus annuus*) seeds harvested in early development (ca. 20 days post anthesis). The seeds were homogenized with a polytron homogenizer in 0.1M tricine and 0.6M glycerol (pH 9.0). Plastids were obtained from this homogenate by procedures similar to those described previously [Guerra, et al., J. Biol. Chem., Vol. 263, (1988), pp. 4386–4391 and Hoj, et al., Carlsberg Res. Commun., Vol. 49, (1984), pp, 483–492]. The homogenate was filtered through a layer of nylon gauze and centrifuged at $4,000 \times g$ for 5 min. The pellet containing the crude plastid preparation was resuspended in 0.1M tricine, 0.3 M glycerol, 2 mM DTT, and 1 mM $MgCl_2$ (pH 9.0), and sonicated for 30 minutes in a Bronson 8200 Ultra Sonicator. After 2 hours of centrifugation at $200,000 \times g$ the supernatant was fractionated with $(NH_4)_2SO_4$. The 45–80% ammonium sulfate fraction (pellet after centrifugation) was dialyzed and used directly as the MCT source.

Fatty Acid Synthetase (FAS) Assays

The enzymatic assay of spinach FAS was performed as previously described and incorporated herein by reference [Rock, et al., J. Biol. Chem., Vol. 254, (1979), pp. 7123–7128]. FAS was isolated from spinach lead chloroplasts. A chloroplast pellet was obtained from spinach leaves in the same manner that the sunflower seed plastic pellet was prepared (as described above). The chloroplasts were resuspended in deionized water and subjected to two freeze thaw cycles in a dry ice-ethanol bath. The suspension was then brought to 1% (v/v) Triton X-100 and gently mixed with an equal volume of 0.2M tricine, 0.6M glycerol, 4 mM DTT, and 2 1 mM $MgCl_2$ (pH 9.0). The lysed chloroplast suspension (complete lysis was verified microscopically) was centrifuged at $200,000 \times g$ for 90 min. The supernatant was brought to 45% (w/v) $NH_4)_2SO_4$ and centrifuged at $10,000 \times g$. The supernatant from this procedure was made 75% (w/v) $NH_4)_2SO_4$ and again centrifuged at 10,000×g. The pellet was dissolved in and dialyzed against 0.1M tricine, 0.3M glycerol and 2 mM DTT (pH 9.0) and used as an FAS source.

EXAMPLE 2

Construction of Gene Fusion

The 268 bp Bam HI fragment of pPB269 carrying the synthetic spinach ACP-I gene, [Beremand, et al., Arch. Biochem. Biophys., Vol. 256, (1987), pp. 90–100] the subject of U.S. Pat. No. 4,888,282 the disclosure of which is incorporated herein by reference, was gel-purified and ligated into the BAM II site of pRIT2T. Insertion in the proper orientation placed the ACP gene downstream of and in frame with the Fc-binding portion of the staphylococcal protein A gene carried on this vector.

In order to avoid the potentially lethal effects of high-level gene expression associated with genes under the control of the $P_R$ promoter [Struhl, K., (1985), Supra] the constructs were introduced into hose cells carrying the temperature-sensitive repressor cI857. Thus, at 30° C. the $P_R$ promoter is repressed but at 42° C. it is induced. Plasmid DNA from transformants was analyzed for proper insert size and then subjected to restriction analysis to determine the orientation of the insert within the vector. Several clones were obtained in the proper orientation and one designated pPB3 was chosen for further study.

Western Blot Analysis of Fusion Protein

Figure 1:
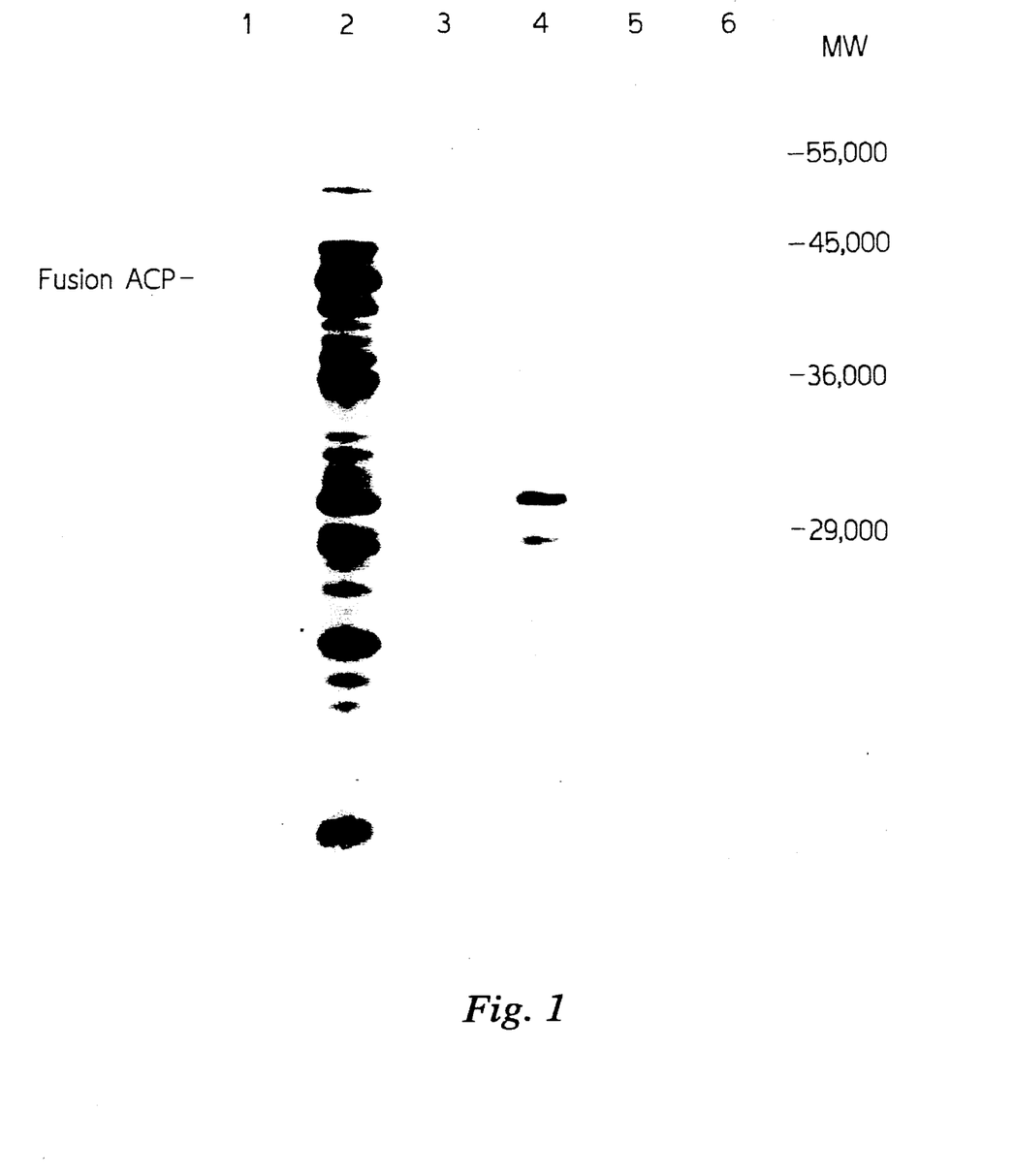

In order to confirm the production of an appropriately sized fusion protein Western blot analysis was carried out on extracts prepared from N4830-1 cells carrying pPB3. Thermal induction was carried out as indicated. Cell extracts were prepared and the proteins separated electrophoretically on a SDS-polyacrylamide gel. A western blot of this gel is shown in FIG. 1. The conditions employed minimized the interaction of $E.$ $coli$ ACP (through blocking with $E.$ $coli$ extracts) with the rabbit antibody. The results in lane 2 indicate the production of a fusion protein of the correct size ($\approx 42$ kDa) that strongly cross reacts with the antibody. Production of this protein is inducible (lanes 1 and 2) and does not occur in the absence of pPB3 (lanes 3 and 4). The smaller bands in lane 2 suggest the occurrence of some proteolytic degradation, although most of the reacting material appears to be in the full-length gene product. The non-specific interaction between IgG and protein A as demonstrated with the truncated 31 kDa protein A molecule (lane 4) necessitated additional experiments to prove that the 42 kDa protein possessed properties of both protein A and ACP. These experiments presented below examined the ability of this protein to bind to IgG and its ability to act as an acyl carrier in ACP-requiring reactions.

IgG Sepharaose Chromatography of ACP-I/Protein A Fusion Protein

Separation was based on the strong binding known to occur between staphylococcal protein A and the Fc portion of IgG molecules [Langone, J. J., "Protein A. of Staphyloccus aureas and related immunoglobulin receptors produced by Streptococci and Pneumococci". In: Dixon, et al. (eds.), Advances in Immunology, Vol. 32, (1982), Academic Press, New York, pp. 157–252]. Crude extracts were prepared as indicated and applied to a column of human IgG crosslinked to Sepharose 6FF. Eluted proteins were subjected to SDS-PAGE.

Figure 2:
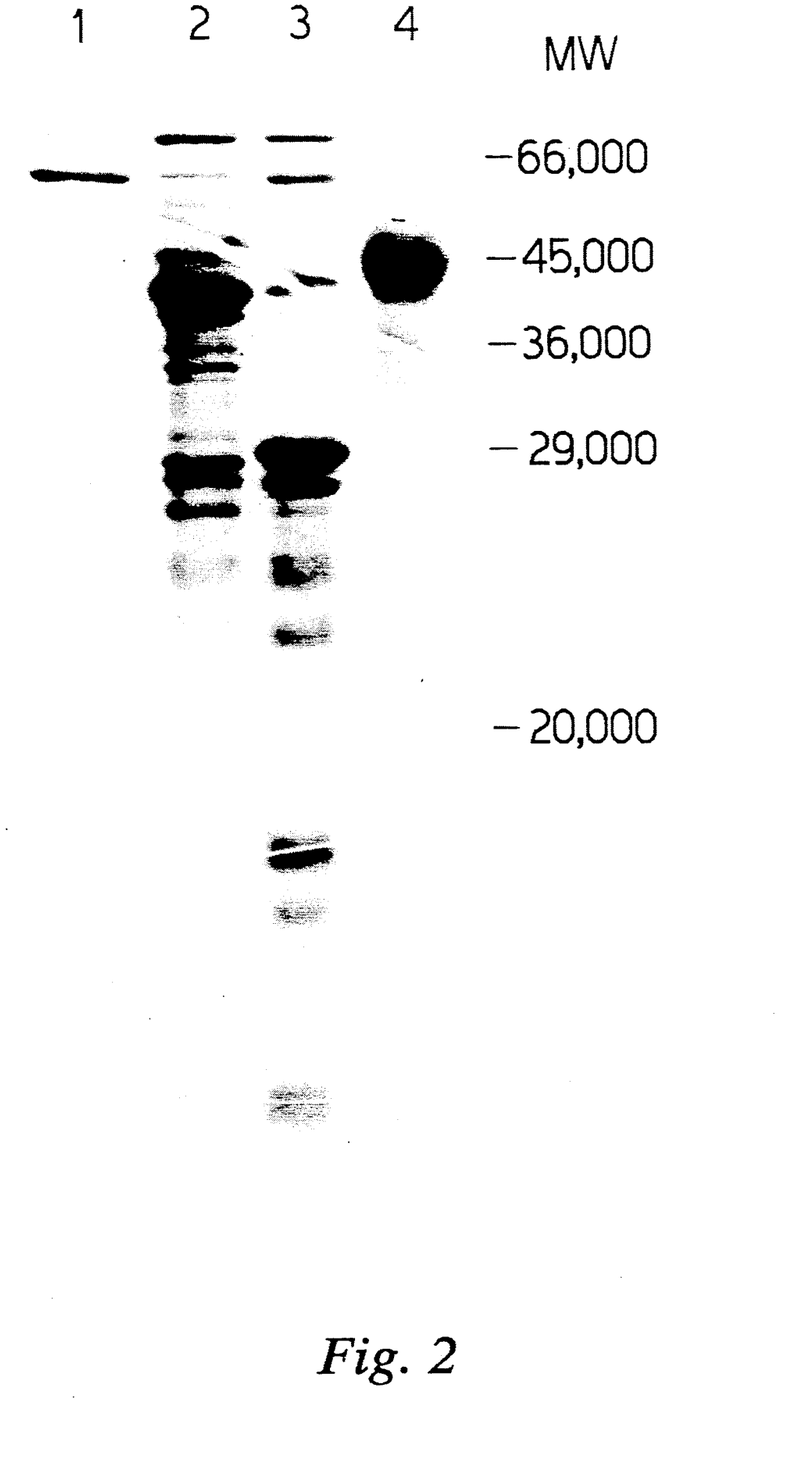

The results shown in FIG. 2 indicate a significant purification of a 42 kDa protein from culture carrying pPB3. This protein is not purified from cultures carrying pR1T2T although a 31 kDa protein representing the truncated protein A molecule is purified. Again, there is some evidence of proteolytic degradation. Relative staining intensity when compared to known amounts of a protein standard indicated that production of at least 75 µg of intact fusion protein per ml of induced culture. This was corroborated by an ELISA assay for protein A content in the eluted fractions. The bands larger than 42 kDa are apparently host cell proteins non-specifically binding to the column matrix as they occasionally appear in eluants from uninfected host cells.

Figure 3:
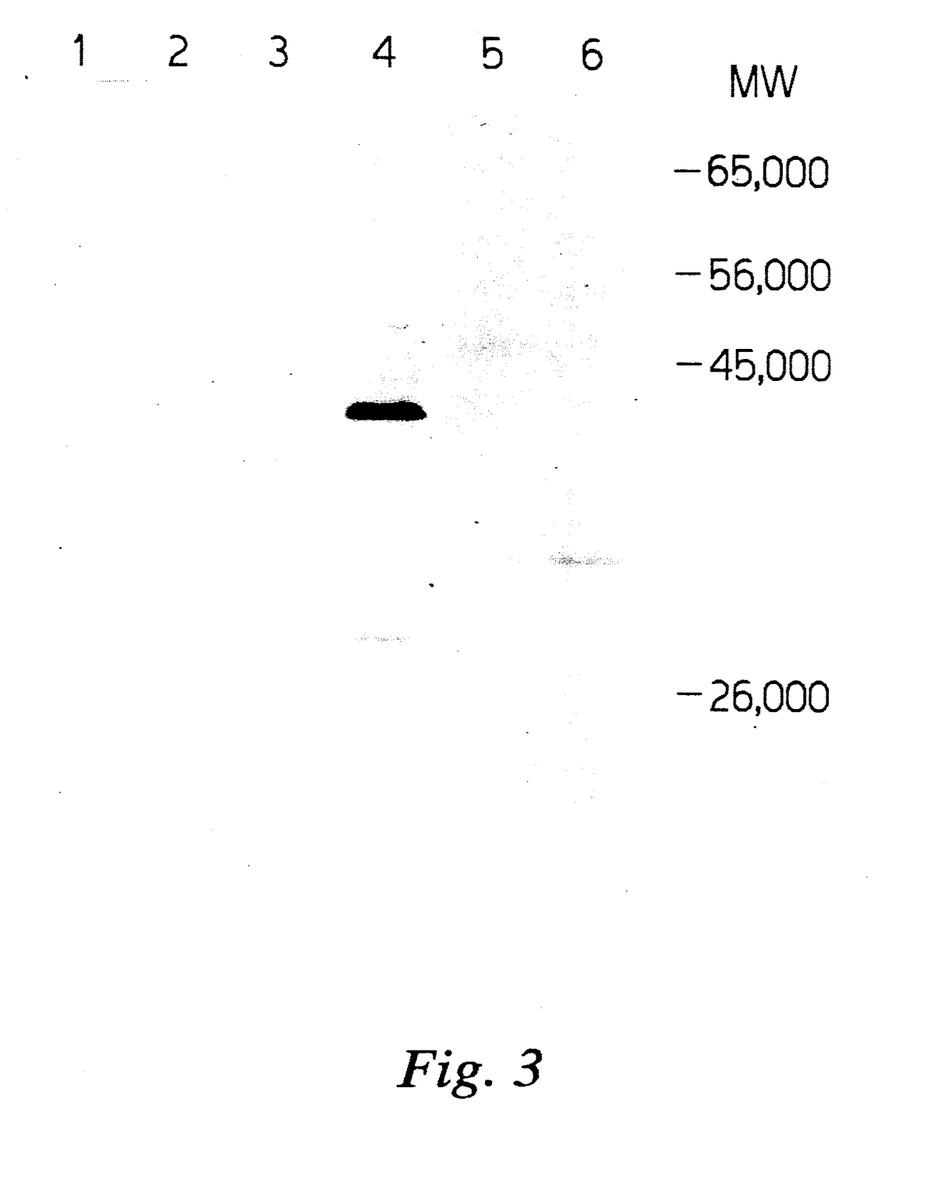

ACP Activity of the Fusion Protein $E.$ $coli$ holo ACP synthetase will attach phosphopantetheine to spinach ACP-I in vivo [Beremand, et al., J. Cellular Biochem., Vol. 11B, (1987), p. 48, and; Beremand, et al., Arch. Biochem. Biophys., Vol. 256, (1987), pp. 90–100]. To determine whether this prosthetic group would be added to the fusion protein, cells carrying pPB3 were labelled with beta-[3-$^3$H] alanine. FIG. 3 indicates that label is incorporated into the 42 kDa fusion protein. Thus, the prosthetic group is added to the fusion protein, presumably at the ACP moiety.

Figure 4:
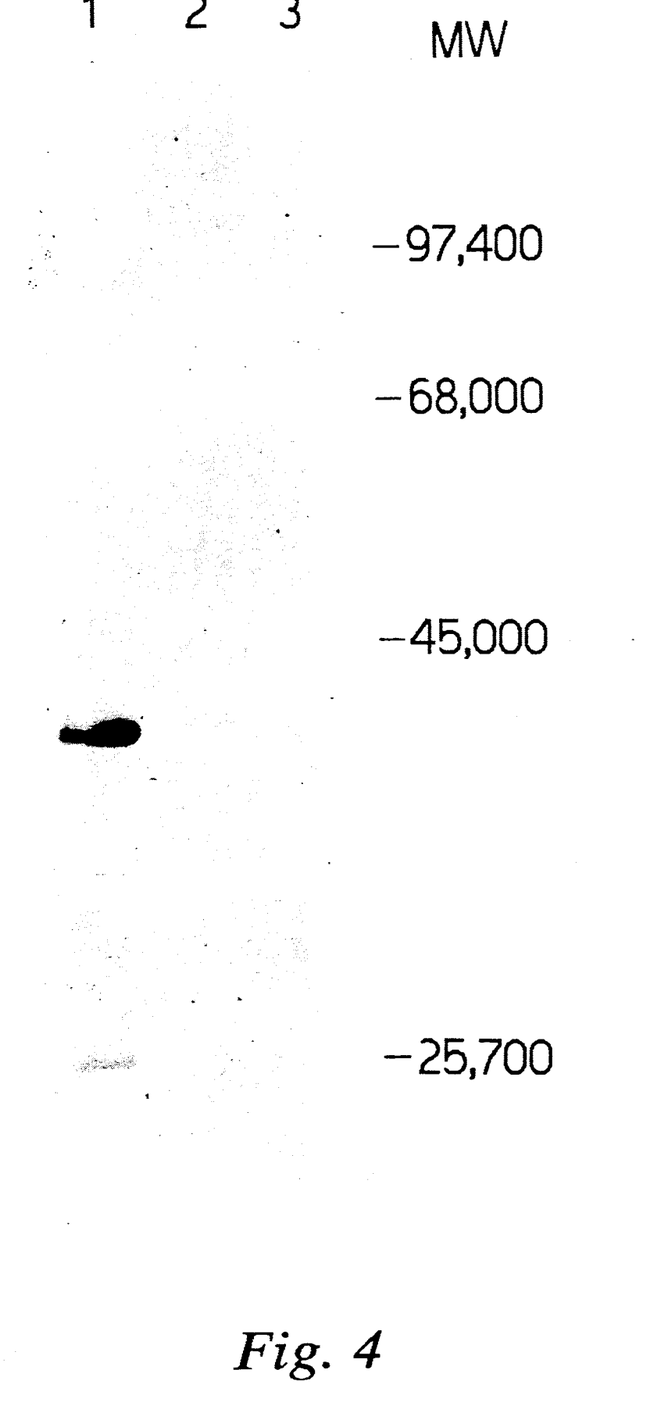

The attachment of the phosphopantetheine group to the fusion protein suggested that it might participate in some ACP requiring enzymatic reactions. IgG sepharose-purified fusion protein was tested for its ability to participate in acyl ACP synthetase reactions in which $^{14}$C-palmitic acid was the substrate. The acyl ACP synthetase reaction products were separated on SDS-polyacrylamide gels. A fluorogram of such a gel is shown in FIG. 4. These results confirm that the fusion protein was being acylated, while the truncated protein A molecule produced by pR1T2T was not.

Figure 5:
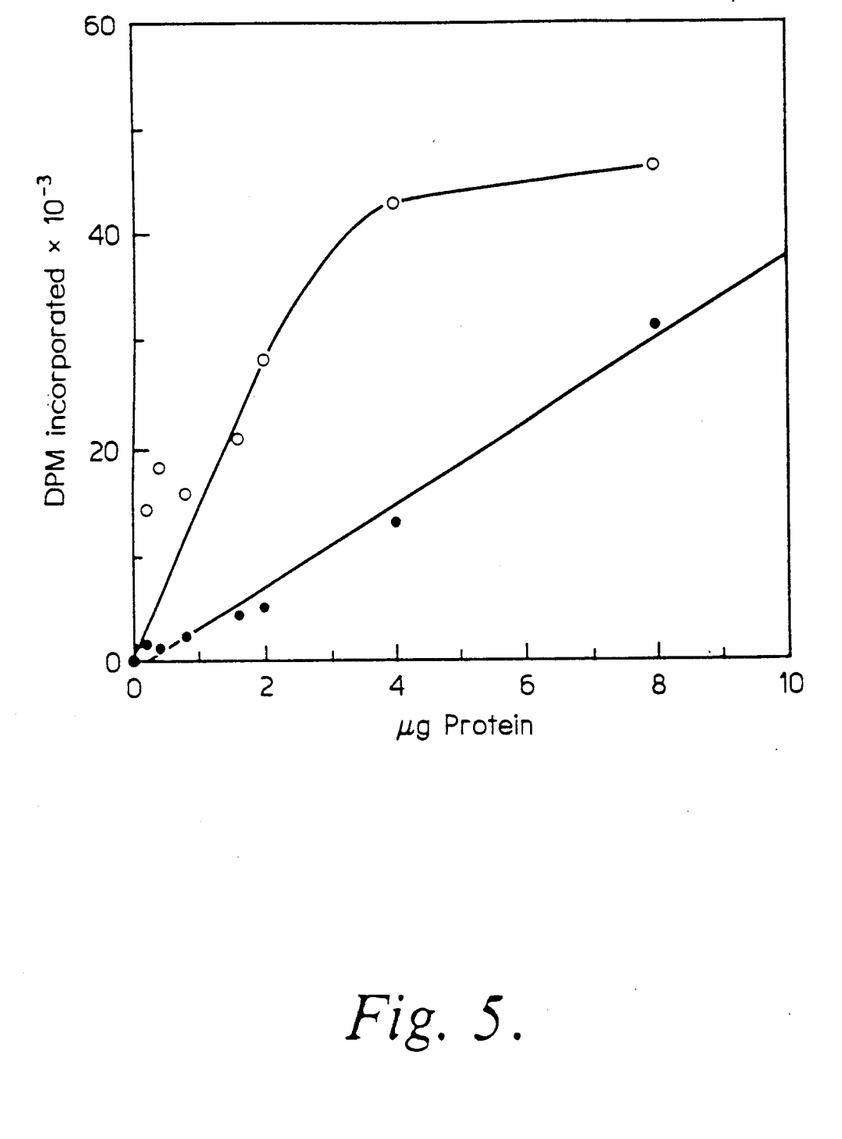

Further analysis of the interaction of the fusion ACP with $E.$ $coli$ acyl ACP synthetase was performed as indicated in FIG. 5. For these experiments the fusion ACP was purified to near homogeneity. The results indicate that, under the conditions employed, the fusion protein was approximately 25% as active as the $E.$ $coli$ ACP on a per weight basis. Since ACP accounts for about 25% of the molecular weight of the fusion protein these results suggest a similar specific activity for the ACP moiety of the fusion protein and the unfused ACP-I.

We examined the interaction of the ACP/protein A fusion protein with one component of plants FAS, malonyl-CoA:ACP transacylase (MCT). Table 1 shows a direct comparison of MCT activity in reactions using ACP-I produced from a synthetic ACP-I gene and in reactions using the fusion protein as cofactor. The results indicate that the fusion protein does participate in the MCT reaction. The optimum ACP/malonyl CoA ratio appears to be shifted for the fusion protein. The fusion protein possesses ½ to ¼ of the activity in the MCT reaction as the unused ACP.

Figure 6:
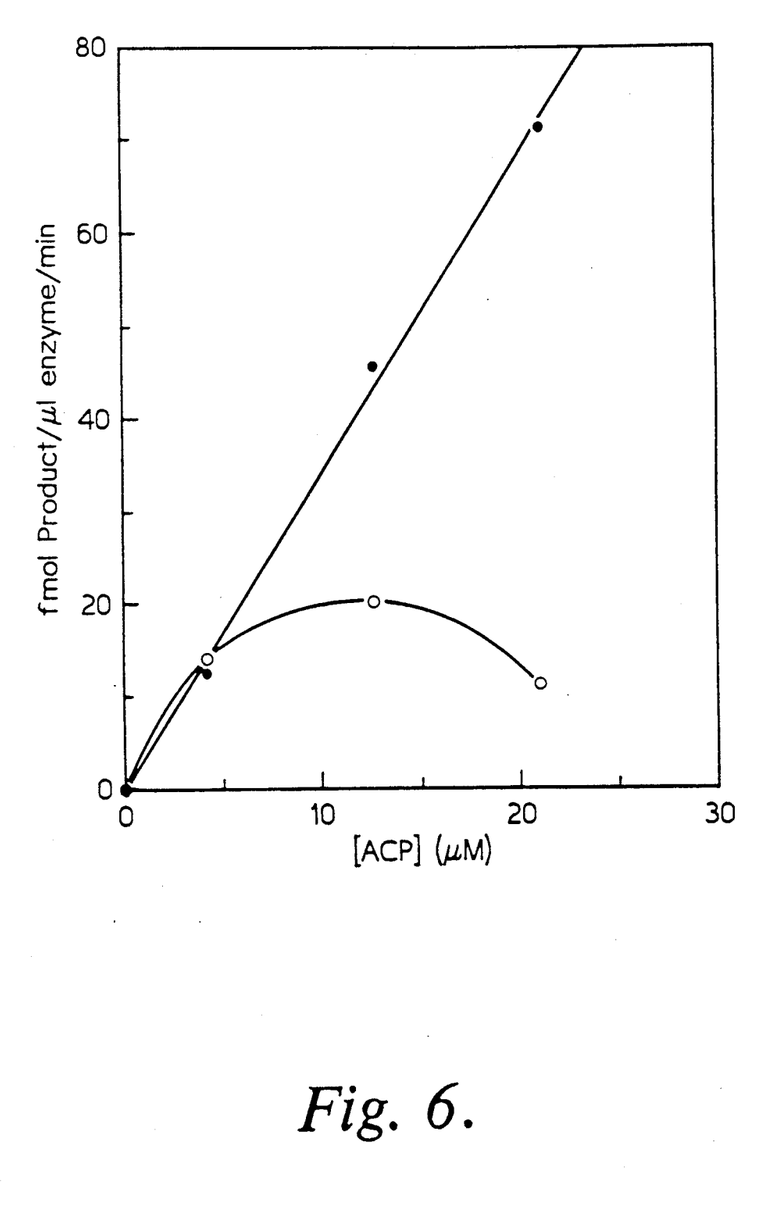
Figure 7:
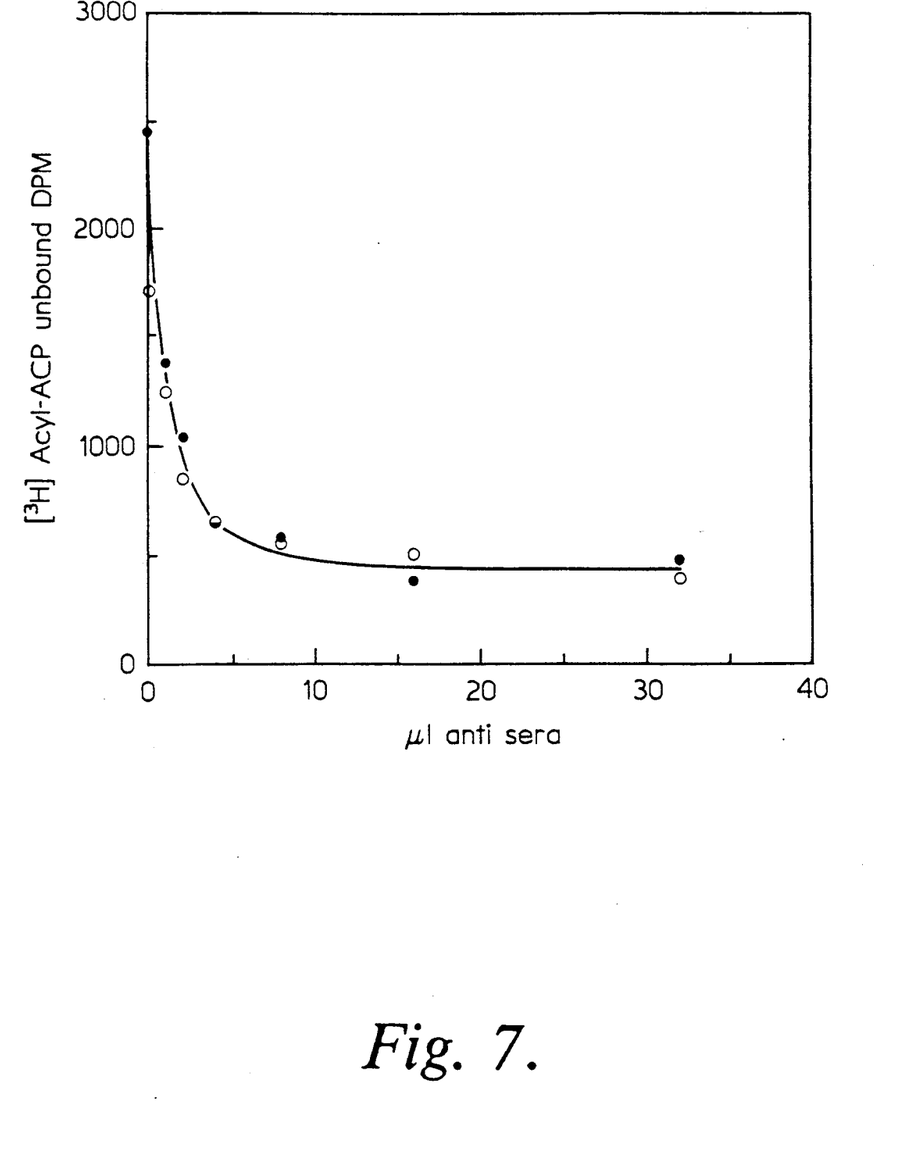
FIG. 7. Comparison of serum raised against the ACP/protein A fusion protein and spinach ACP. Radioimmunoassays were performed as described by Kuo et al., Anal. Biochem., Vol. 136, (1984), pp. 479-502, on authentic spinach ACP-I by using identical dilutions of antiserum prepared against authentic ACP-I (○) and the ACP/protein A fusion protein (●).

The biosynthetic reactivity of the fusion ACP in in vitro fatty acid synthesis was examined for spinach leaf extracts. FIG. 6 compares the activity of the ACP-I protein A fusion to unfused ACP at a variety of concentrations. The data indicate that the spinach fatty acid synthesis machinery is indeed able to utilize the fusion ACP at least as well as it does the unfused ACP. Furthermore, the inhibitory effects of excess ACP, seen with the unfused ACP, do not occur with the ACP/-protein A fusion. In other experiments (data not shown), the fusion ACP was nearly unreactive in an *E. coli* fatty acid synthesis reaction. We have made similar observation on the activity of the unfused spinach ACP-I gene product with *E. coli* FAS [Guerra, et al., (1988), Supra].

TABLE I

| Malonyl-CoA:ACP transacylase (MCT) activity | | |
|---|---|---|
| ACP Source | ACP Concentration (mol/l) | MCT Activity (pmol/l min) |
| R-ACP-I | 8.24 | 9.0 |
| R-ACP-I | 24.7 | 60.6 |
| R-ACP-I | 41.2 | 40.5 |
| F-ACP | 8.24 | 1.2 |
| F-ACP | 24.7 | 9.2 |
| F-ACP | 41.2 | 13.7 |

MCT was isolated from sunflower as shown above. Reactions were started by the addition of ACP. Each reaction contained 1 mM malonic acid, 25 mM tricine (pH 8.0) 8.24M [2-$^{14}$C]malonyl-CoA, 10.5 mM DTT, 75 mM glycerol and enzyme. Reactions were carried out at 20° C. for 1 min, then stopped with the addition of 20% TCA (4° C.). Precipitated [$^{14}$C]malonyl-ACP was isolated on DE81 filter discs and radioactivity was determined. R-ACP-I is the protein produced in *E. coli* from the synthetic spinach ACP-I gene carried on the plasmid pPB104 [Nilsson, et al., (1985), Supra]. F-ACP is the protein A/ACP-I fusion protein.

Purification of FAS Enzymes

The purified protein A:acyl carrier protein-I (A:ACPI) can be easily immobilized to human IgG-linked agarose or sepharose. This antibody-ligand matrix can then be used as an affinity column to purify fatty acid conformationally available to link with FAS enzymes which utilize ACP or ACP thioesters as substrates. Crude plant extracts can be passed through the IgG-protein A:ACPI matrix under lower ionic strength and neutral pH solvent conditions. This will allow the formation of a FAS enzyme-ACPI affinity stabilized immobilization complex. The FAS enzyme is then eluted with either reducing agent (e.g., 100 mM DTT), protein A:ACPI, ACP-I or acyl ACP-I, depending upon the native substrate which reacts with the given immobilized enzyme. This procedure should greatly amplify purification and increase yield of the dozen FAS enzymes which utilize ACP from crude plant extracts. Thus human IgG protein A:ACPI affinity chromatography protocol represents a significant improvement over previous ACP affinity columns which typically show poor binding capacity and unacceptable resolution. Due to the unique linkage of the ACP-I moiety to protein A and the specific binding of protein A to human IgG, no interaction or partial shielding of ACP reactive domans will occur.

It can be seen there has been provided by the foregoing detailed description a recombinant DNA, methods for the production of a gene fusion product and methods of purification. From this description many alternatives and variations may be practiced. It is intended that the spirit and scope of the instant invention encompass all such alternatives and variations.

We claim:

1. A recombinant DNA which encodes a plant acyl carrier protein and the $F_c$-binding portion of staphylococcal protein A, wherein the recombinant DNA comprises a first sequence encoding the acyl carrier protein gene downstream and in frame with a second DNA sequence encoding the $F_c$-binding portion of staphylococcal protein A.

2. A recombinant DNA of claim 1, wherein the plant acyl carrier protein is a spinach acyl carrier protein.

3. A recombinant DNA of claim 2, wherein the spinach acyl carrier protein is spinach acyl carrier protein-I-Gly$^{76}$.

4. The recombinant DNA of claim 3 wherein said protein is further characterized in that the level of fatty acid synthetase activity is approximately proportional to the level of acyl carrier protein throughout the range of from 0 to about 20 μM.

5. A recombinant DNA construct comprising a first DNA sequence which encodes a plant acyl carrier protein and a second DNA sequence which encodes the $F_c$-binding portion of staphylococcal protein A, wherein the first DNA encoding the acyl carrier protein gene is downstream and in frame with the DNA encoding the $F_c$-binding portion of staphylococcal protein A.

6. The construct of claim 5, wherein said construct is a plasmid.

7. The construct of claim 5, wherein said construct is a cloning vector.

8. The construct of claim 5, wherein said construct is an expression vector.

9. The recombinant DNA construct of claim 5, wherein the plant acyl carrier protein is a spinach acyl carrier protein.

10. The construct of claim 9, wherein said construct is a plasmid.

11. The construct of claim 9, wherein said construct is a cloning vector.

12. The construct of claim 9, wherein said construct is an expression vector.

13. The recombinant DNA construct of claim 9, wherein the plant acyl carrier protein is spinach acyl carrier protein-I-Gly$^{76}$.

14. The construct of claim 13, wherein said construct is a plasmid.

15. The construct of claim 13, wherein said construct is a cloning vector.

16. The construct of claim 13, wherein said construct is an expression vector.

17. The recombinant DNA construct of claim 13 wherein said protein is further characterized in that the level of fatty acid synthetase activity is approximately proportional to the level of acyl carrier protein throughout the range of from 0 to about 20 μM.

18. A phase comprising the recombinant DNA construct of claim 16.

19. A method of producing an enzymatically active acyl carrier protein bound to the $F_c$-binding portion of staphylococcal A protein comprising:
   a. transforming cells for expressing said protein with an expression vector carrying a recombinant DNA comprising a first sequence encoding the acyl carrier protein gene downstream and in frame with a second DNA sequence encoding the $F_c$-binding portion of staphylococcal protein A; and
   b. culturing said cells under conditions wherein said proteins are expressed.

20. The method of claim 19 wherein the protein is spinach acyl carrier protein-I-Gly$^{76}$ characterized in that the level of fatty acid synthetase activity is approximately proportional to the level of acyl carrier protein throughout the range of from 0 to about 20 μM.

* * * * *